United States Patent [19]
Bird et al.

[11] Patent Number: 5,659,121
[45] Date of Patent: Aug. 19, 1997

[54] DNA, DNA CONSTRUCTS, CELLS AND PLANTS DERIVED THEREFROM

[75] Inventors: Colin Roger Bird, Berkshire; Donald Grierson, Loughborough; Lisa Naomi Hall, West Midlands, all of England

[73] Assignee: Zeneca Limited, London, England

[21] Appl. No.: 256,130

[22] PCT Filed: Dec. 18, 1992

[86] PCT No.: PCT/GB92/02355
§ 371 Date: Sep. 30, 1994
§ 102(e) Date: Sep. 30, 1994

[87] PCT Pub. No.: WO93/13212
PCT Pub. Date: Jul. 8, 1993

[30] Foreign Application Priority Data

Dec. 20, 1991 [GB] United Kingdom ............... 9127098

[51] Int. Cl.⁶ .................. A01H 4/00; C12N 15/82; C12N 5/14; C12N 15/29
[52] U.S. Cl. ........... 800/205; 800/255; 800/DIG. 44; 536/23.2; 435/320.1; 435/411; 435/419
[58] Field of Search .............. 536/23.2; 435/320.1, 435/240.4, 172.3; 800/205, 255, DIG. 44

[56] References Cited

U.S. PATENT DOCUMENTS 5,073,676 12/1991 Bridges et al. ............... 800/205
5,447,867 9/1995 Bridges et al. ............... 435/320.1

FOREIGN PATENT DOCUMENTS 271988 6/1988 European Pat. Off. .

OTHER PUBLICATIONS

Harriman et al. (May 1990) Plant Physiol. vol. 93, No. 1, p. 44, abstract 249.
Harriman et al. (1991) Plant Physiology vol. 97 (1) pp. 80–87.
Boswell et al in COMPUTATIONAL MOLECULAR BIOLOGY SOURCES AND METHODS FOR SEQUENCE ANALYSIS (Lesk, ed.) Oxford University Press, Oxford, 1988.
WO,A,9 108 299 (ICI) 13 Jun. 1991, see claims 15; examples 17–24.
Harriman, et al: "Identification and characterization of three pectin methylesterase genes in tomato" PLANT PHYSIOLOGY, vo. 93, No. 1, May 1990, p. 44 –see abstract 249.
Harriman: "Molecular clining and expression of pectin methylesterase, genes in Lycopersicon esculentum (tomato)" CHEMICAL ABSTRACTS, vol. 114, 1991, abstract No. 96207. & PHD THESIS, PURDUE UNIVERSITY, vol. 51, No. 6, 1990, p. 2702.
Harriman et al:, "Molecular cloning of tomato pectin methylesterase gene and its expression in rutgers, ripening inhibitor, nonripening, and never ripe tomato fruits", PLANT PHYSIOLOGY (1991) vol. 97, No. 1, pp. 80–87, see FIG. 2A.
Tieman, et al: "Inhibition of pectin methylesterase (PME) gene expressioin in transgenic tomato fruit by anti–sense RNA", J. CELL.BIOCHEM.SUPPL.KEYSTONE SYMPOSIUM, vol. 15A, 1991, p. 81, see abstract A353.

*Primary Examiner*—Che S. Chereskin
*Attorney, Agent, or Firm*—Cushman Darby & Cushman IP Group of Pillsbury Madison & Sutro, LLP

[57] ABSTRACT

DNA constructs comprise a DNA sequence homologous to some or all of the pectinesterase gene encoded by the clone pB8 (Sequence ID No.1), under control of a transcriptional initiation region operative in plants for transcribing this DNA sequence, optionally in the antisense direction to produce RNA complementary to the gene mRNA. From such constructs may be derived transformed plant cells and plants in which expression of pectinesterase genes is inhibited: fruit from the plants (such as tomatoes) can show modified ripening properties.

16 Claims, No Drawings

DNA, DNA CONSTRUCTS, CELLS AND PLANTS DERIVED THEREFROM

This invention relates to novel DNA constructs, plant cells containing the constructs and plants derived therefrom. In particular it involves the use of antisense or sense RNA technology to control gene expression in plants.

During tomato fruit ripening, the components of the cell walls undergo a series of modifications. The pectin component is subject so substantial modification and degradation. The major changes to the pectin include: solubilisation, depolymerisation and demethylation. The changes in texture of the fruit that occur during ripening occur in parallel with the changes to the pectin component. It has been demonstrated that many of these changes are the result of the action of enzymes in the cell wall.

The cell wall enzymes polygalacturonase and pectin esterase have a major role in modifying pectin during fruit ripening. Individual cDNA clones that corresponded to mRNAs encoding these two enzymes have previously been identified and characterised. DNA sequences from these clones have been used to demonstrate sense and antisense inhibition of these enzymes (EPA 271,988, ICI). For antisense inhibition of, say, pectin esterase, a fragment of DNA coding for the mRNA that produces pectinesterase is inserted into the plant genome under control of a plant promoter, but in reverse orientation. In this way the plant produces RNA sequences complementary to the mRNA that is translated into pectin esterase: and this interferes in some way with the translation of the mRNA into protein. For sense inhibition of, say, polygalacturonase, a fragment of DNA coding for the mRNA that produces polygalacturonase is inserted into the plant genome under control of a plant promoter, in normal orientation. The plant produces RNA sequences homologous with part of the full-length mRNA that is translated into polygalacturonase. Again, this interferes with and can substantially inhibit the translation of polygalacturonase mRNA into protein. How this happens is not clear.

In this invention, we provide clones comprising further novel DNA coding sequences from a new pectin esterase gene. These can be used to make DNA constructs that will control expression of pectinesterase, either by sense or antisense inhibition.

In work leading to the invention, we have identified a novel cDNA (pB8) which encodes a tomato pectin esterase isoenzyme. The cDNA was identified in a clone from a library constructed using mRNA isolated from tomatoes at an early ripening stage. The cDNA in the clone was approximately 2 kb long. Characterisation of the sequence of the clone indicated in addition to sequences similar to those found in the previously characterised cDNA sequence (pPE1), there was also a 358 bp extension at the 5' end. This extended sequence was not predicted since the size of the previous cDNA (pPE1–1.655 kb) corresponded to the determined size of the mRNA (1.6 kb). More recent, unpublished determinations indicate that the true size of the PE mRNA in tomato fruit is approximately 2.0 kb (and see Handa, 1992).

According to the present invention, we further provide recombinant DNA comprising an upstream promoter base sequence, a base sequence for transcription into mRNA under control of said upstream promoter base sequence, and a downstream transcription terminator base sequence, characterised in that the base sequence for transcription comprises a sequence of bases complementary to a substantial run of bases in the novel PE cDNA sequence. The sequence for transcription may be oriented in the normal or reverse sense, so as to produce either sense or antisense RNA in plants. The invention also includes plant cells containing such constructs; plants derived therefrom showing modified ripening characteristics; seeds of such plants; and novel recombinant DNA from clones B8 and B16.

DNA constructs according to the invention comprise a base sequence for transcription at least 10 bases in length. For antisense transcription at least, there is no theoretical upper limit to the base sequence—it may be as long as the relevant mRNA produced by the cell—but for convenience it will generally be found suitable to use sequences between 100 and 1000 bases in length. For sense transcription, it may be found that sequences approaching the full length of the corresponding mRNA may lead to over-production of the enzyme rather than inhibition. Where this happens shorter sequences should be used, unless over-production is desired. The preparation of suitable constructs is described in more detail below.

The preferred DNA for use in the present invention is DNA derived from the clone B8. The required antisense DNA can be obtained in several ways: by cutting with restriction enzymes an appropriate sequence of such DNA; by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the cut DNA sequence is inverted with respect to its orientation in the strand from which it was cut.

In new vectors expressing antisense RNA, the strand that was formerly the template strand becomes the coding strand, and vice versa. The new vector will thus encode RNA in a base sequence which is complementary to the sequence of pB8 mRNA. Thus the two RNA strands are complementary not only in their base sequence but also in their orientations (5' to 3').

As source of the DNA base sequence for transcription, it is convenient to use cDNA clones such as pB8. The base sequences of pB8 are set out in Table 1. pB8 has been deposited on 06 Dec. 1991 with the National Collections of Industrial and Marine Bacteria, Aberdeen, under Accession No. NCIB 40463. Alternatively, cDNA clones similar to pB8 may be obtained from the mRNA of ripening tomatoes by the methods similar to that described by Slater et al, Plant Molecular Biology 5, 137–147, 1985. In this way may be obtained sequences coding for the whole, or substantially the whole, of the mRNA produced by pB8. Suitable lengths of the cDNA so obtained may be cut out for use by means of restriction enzymes.

As previously stated, DNA suitable for use in the present invention is DNA showing homology to the gene encoded by the clone pB8. pB8 was derived from a cDNA library isolated from early ripening tomato RNA.

An alternative source of DNA for the base sequence for transcription is a suitable gene encoding the pectinesterase mRNA represented in pB8. Such a gene may be isolated, for example, by probing tomato DNA with cDNA from clone pB8. This gene may differ from the cDNA of, e.g. pB8 in that introns may be present. The introns are not transcribed into mRNA (or, if so transcribed, are subsequently cut out). When using such a gene as the source of the base sequence for transcription it is possible to use either intron or exon regions.

A further way of obtaining a suitable DNA base sequence for transcription is to synthesise it ab initio from the appropriate bases, for example using Table 1 as a guide.

Recombinant DNA and vectors according to the present invention may be made as follows. A suitable vector containing the desired base sequence for transcription (for example pB8) is treated with restriction enzymes to cut the sequence out. The DNA strand so obtained is cloned desired, in reverse orientation) into a second vector containing the desired promoter sequence (for example cauliflower mosaic virus 35S RNA promoter or the tomato polygalacturonase gene promoter sequence—UK Patent Application 9024323.9) and the desired terminator sequence (for example the 3' of the *Agrobacterium tumefaciens* nopaline synthase gene, the nos 3' end).

According to the invention we propose to use both constitutive promoters (such as cauliflower mosaic virus 35S RNA) and inducible or developmentally regulated promoters (such as the ripe-fruit-specific polygalacturonase promoter) as circumstances require. Use of a constitutive promoter will tend to affect functions in all parts of the plant: while by using a tissue-specific promoter, functions may be controlled more selectively. Thus in applying the invention, e.g. to tomatoes, it may be found convenient to use the promoter of the PG gene (UK Patent Application 9024323.9, filed 8 Nov. 1990). Use of this promoter, at least in tomatoes, has the advantage that the production of antisense RNA is under the control of a ripening-specific promoter. Thus the antisense RNA is only produced in the organ in which its action is required. Other ripening-specific promoters that could be used include the E8 promoter (Diekman & Fischer, 1988 cited above). It may be advantageous to use a ripening-specific promoter that switches on in unripe fruit, so as to leinhibit the formation of pectinesterase from then on.

Vectors according to the invention may be used to transform plants as desired, to make plants according to the invention. Dicotyledonous plants, such as tomato and melon, may be transformed by *Agrobacterium* Ti plasmid technology, for example as described in EP 271,988 (ICI). Such transformed plants may be reproduced sexually, or by cell or tissue culture.

The degree of production of sense or antisense RNA in the plant cells can be controlled by suitable choice of promoter sequences, or by selecting the number of copies, or the site of integration, of the DNA sequences according to the invention that are introduced into the plant genome. In this way it may be possible to modify ripening or senescence to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Such plants have modified fruit ripening properties. Examples of genetically modified plants according to the present invention include, as well as tomatoes, fruits of such plants as mangoes, peaches, apples, pears, strawberries, bananas and melons.

Tomatoes with reduced pectin esterase activity give improved characteristics in paste made from the processed tomatoes: in particular increased viscosity of the serum from the paste and decreased granularity of the paste, which eventually gives a smoother and more glossy paste.

The invention will now be described further with reference to Table 1, which shows the full base sequence of the clone pB8 (SEQ ID No:1) and, for comparison, the base sequence of the clone pB16 (SEQ ID No:2), homologous to the pectinesterase gene disclosed in EPA 271,988.

The following Examples illustrate aspects of the invention.

EXAMPLE 1

Identification and Characterisation of Novel PE cDNA

A cDNA library in lambda zapII (Stratagene) which had been prepared from mRNA extracted from early ripening tomato fruit was screened with a radiolabelled oligonucleotide probe corresponding to a sequence from the 5' end of pPE1 (Ray et al 1988). Several hybridising clones were identified and plasmid DNA was excised in vivo according to the instructions supplied by Stratagene. The sizes of the cDNA inserts in the clones were determined by digestion with BamH1 and KpnI followed by agarose gel electrophoresis. One clone (pB8) had an insert size of approximately 2 kb. This clone was selected for further analysis since the insert was approximately 300 bases longer than that of the previously identified PE cDNA (pPE1). The nucleotide sequence of the 5' 530 bases of this clone were determined. The 5' end of pPE1 was located at base 359 of the new clone.

EXAMPLE 2

Construction of a Constitutively Expressed PE Antisense Vector

A plant transformation vector is constructed using the sequences corresponding to bases 1 to 338 of pB8 (FIG. 1). This fragment is synthesised by polymerase chain reaction using synthetic primers. The fragment is cloned into the vector pJR1 which is previously cut with SmaI. pJR1 (Smith et al Nature 334, 724–726, 1988) is a vector hased on Bin19 (Bevan, Nucleic Acids Research, 12, 8711–8721, 1984), which permits the expression of the antisense RNA under the control of the CaMV 35S promoter. This vector includes a nopaline synthase (nos) 3' end termination sequence.

After synthesis of the vector, the structure and orientation of the PE sequences is confirmed by DNA sequence analysis.

EXAMPLE 3

Construction of a Developmentally Regulated PE Antisense Vector

The fragment of the pB8 cDNA that was described in example 2 is also cloned into the vector pJR3.

pJR3 is a Bin19-based vector, which permits the expression of the antisense RNA under the control of the tomato polygalacturonase promoter. This vector includes approximately 5 kb of promoter sequence and 1.8 kb of 3' sequence from the PG promoter separated by a multiple cloning site.

After synthesis, vectors with the correct orientation of pB8 sequences are identified by DNA sequence analysis.

EXAMPLE 4

Construction of a Constitutively Expressed PE Sense Vector

The fragment of pB8 cDNA that was described in example 2 is also cloned into the vector pJR1 in the sense orientation.

After synthesis, the vectors with the sense orientation of pB8 sequence are identified by DNA sequence analysis.

EXAMPLE 5

Construction of a Developmentally Regulated PE Sense Vector

The fragment of pB8 cDNA that was described in example 2 is also cloned into the vector pJR3 in the sense orientation.

After synthesis, the vectors with the sense orientation of pB8 sequence are identified by DNA sequence analysis.

EXAMPLE 6

Production of Genetically Modified Tomato Plants

Vectors are transferred to *Agrobacterium* tumefaciens LBA4404 (a micro-organism widely available to plant biotechnologists) and are used to transform tomato plants. Transformation of tomato stem segments follow standard protocols (e.g. Bird et al Plant Molecular Biology 11, 651–662, 1988—leaf or cotyledon segments may also be used). Transformed plants are identified by their ability to grow on media containing the antibiotic kanamycin. Plants are regenerated and grown to maturity. Ripening fruit are analysed for reduced PE activity and improved fruit quality characteristics.

TABLE 1

| SEQ ID NO: | 1 | | | | | | |
|---|---|---|---|---|---|---|---|
| SEQUENCE TYPE: | Nucleotide | | | | | | |
| SEQUENCE LENGTH: | 1989 | | | | | | |
| STRANDEDNESS: | Single | | | | | | |
| TOPOLOGY: | Linear | | | | | | |
| MOLECULE TYPE: | DNA | | | | | | |
| ORIGINAL SOURCE ORGANISM: | | | Tomato var Ailsa Craig | | | | |
| IMMEDIATE EXPERIMENTAL SOURCE: | | | cDNA clone B8 | | | | |
| FEATURES: | | | | | | | |

| From 16 to 1654 | Open reading frame encoding Pectin Esterase | | | | | | |
|---|---|---|---|---|---|---|---|
| From 16 to 703 | Coding region for N-terminal extension | | | | | | |
| PROPERTIES: | CDNA for tomato fruit pectin esterase | | | | | | |
| TTGCAAACTT | CTAAAATGGC | TAATCCTCAA | CAACCTTTCT | TAATAAAAAC | ACACAAACAA | | 60 |
| AATCCAATAA | TCAGCTTCAA | GATCCTCAGT | TTTGTTATAA | CTTTGTTTGT | TGCTCTCTTC | | 120 |
| TTAGTTGCTC | CATATCAAGT | TGAGATTAAA | CATTCTAATC | TATGTAAAAC | TGCACAAGAT | | 180 |
| TCCCAACTCT | GTCTCAGTTA | TGTCTCTGAT | TTGATATCCA | ATGAAATTGT | CACAACAGAA | | 240 |
| TCAGATGGAC | ATAGTATTCT | GATGAAATTT | TTAGTTAACT | ATGTCCATCA | AATGAACAAT | | 300 |
| GCAATTCCAG | TGGTTCGCAA | AATGAAGAAT | CAGATCAATG | ACATTCGTCA | ACACGGGCT | | 360 |
| TTAACTGATT | GTCTTGAGCT | TCTTGATCAG | TCAGTTGATT | TCGCATCTGA | TTCAATTGCA | | 420 |
| GCAATTGATA | AAAGAAGTCG | CTCGGAGCAT | GCCAATGCGC | AAAGTTGGCT | AAGTGGTGTG | | 480 |
| CTTACTAACC | ACGTTACGTG | CTTGGATGAG | CTTGATTCCT | TTACTAAAGC | TATGATAAAT | | 540 |
| GGAACGAATC | TTGAAGAGTT | GATCTCGAGA | GCTAAGGTAG | CATTAGCGAT | GCTTGCGTCT | | 600 |
| TTGACAACTC | AGGATGAGGA | TGTTTTCATG | ACGGTTTTAG | GAAAAATGCC | ATCTTGGGTG | | 660 |
| AGTTCGATGG | ATAGGAAGCT | GATGGAGAGT | TCGGGTAAGG | ACATTATAGC | GAATGCAGTG | | 720 |
| GTGGCACAAG | ATGGAACGGG | GGATTATCAA | ACACTTGCTG | AAGCAGTTGC | TGCAGCACCA | | 780 |
| GATAAGAGTA | AGACGCGTTA | TGTAATTTAT | GTAAAGAGGG | GAACTTATAA | AGAGAATGTT | | 840 |
| GAGGTGGCTA | GCAATAAAAT | GAACTTGATG | ATTGTTGGTG | ATGGAATGTA | TGCTACGACC | | 900 |
| ATTACTGGTA | GCCTTAATGT | TGTCGATGGA | TCAACAACCT | TCCGCTCTGC | CACTCTTGCT | | 960 |
| GCAGTCGGCC | AAGCATTTAT | ACTACAGGAC | ATATGTATAC | AGAACACAGC | AGGGCCAGCG | | 1020 |
| AAAGACCAAG | CAGTGGCACT | TCGAGTTGGA | GCTGATATGT | CTGTCATAAA | TCGTTGTCGT | | 1080 |
| ATCGATGCTT | ATCAAGACAC | CCTTTATGCA | CATTCTCAAA | GGCAATTCTA | TCGAGACTCC | | 1140 |
| TACGTGACAG | GTACTGTTGA | TTTCATATTT | GGTAATGCAG | CAGTTGTATT | CCAGAAATGC | | 1200 |
| CAGCTCGTAG | CTAGAAAACC | GGGTAAAATAC | CAGCAAAACA | TGGTGACTGC | ACAAGGCAGG | | 1260 |
| ACGGACCCAA | ATCAGGCCAC | GGGGACATCA | ATTCAGTTCT | GTAACATAAT | AGCAAGTTCG | | 1320 |
| GACCTAGAAC | CAGTCCTGAA | AGAATTCCCA | ACATATCTTG | GTAGGCCATG | GKAAGAATAT | | 1380 |
| TCAAGAACTG | TAGTGATGGA | ATCATACTTA | GGTGGTCTCA | TTAATCCAGC | GGGTTGGGCT | | 1440 |
| GAGTGGGACG | GAGATTTTGC | GTTGAAGACA | TTGTATTATG | GTGAATTTAT | GAACAATGGA | | 1500 |
| CCTGGTGCTG | GTACTAGTAA | GCGTGTCAAG | TGGCCTGGTT | ATCATGTCAT | TACTGATCCC | | 1560 |
| GCTAAAGCTA | TGCCGTTCAC | TGTGGCTAAG | CTGATTCAGG | GCGGATCATG | GTTGAGGTCT | | 1620 |
| ACTGGCGTGG | CGTATGTGGA | TGGATTATAT | GATTAGAGTA | TATATATGAT | GTGCCACATG | | 1680 |
| AGCAGGGCAG | AGCAAGCATA | ACACACAACT | CTAGTGTGAC | AAGCATTTAC | ATGGCTCATT | | 1740 |
| CGTTACTACT | AAGTTGTCAA | TAAGTTCTGT | TTAGGGGTTC | ATAAGTTTAT | ATACGTATAT | | 1800 |
| ACATTTACAT | TGGTGATGAA | GCTGAAACTG | ATGATGCTTT | AATGTAATTA | TAGTTTTCTG | | 1860 |
| AAAAAGGATA | TGAGTAATAT | TAGTTTTTCC | CAGATGTGTA | TGGTTGTGGA | ACTGTTTATG | | 1920 |
| CTTAAATTGG | CAAGGGGTAT | TGAATAAAAA | TCTATTGTGT | TAAAAAAAAA | AAAAAAAAAA | | 1980 |
| AAAAAAAAAA | | | | | | | 1989 |

TABLE 2

| SEQ ID NO: | 2 | | | | | |
|---|---|---|---|---|---|---|
| SEQUENCE TYPE: | Nucleotide | | | | | |
| SEQUENCE LENGTH: | 2059 | | | | | |
| STRANDEDNESS: | Single | | | | | |
| TOPOLOGY: | Linear | | | | | |
| MOLECULE TYPE: | DNA | | | | | |
| ORIGINAL SOURCE ORGANISM: Tomato var Ailsa Craig | | | | | | |
| IMMEDIATE EXPERIMENTAL SOURCE: cDNA clone B16 | | | | | | |
| FEATURES: | | | | | | |

| From 13 to 1672 | Open reading frame encoding Pectin Esterase | | | | | |
|---|---|---|---|---|---|---|
| From 13 to 711 | Coding region for N-terminal extension | | | | | |
| Base 368 | Start of cDNA pPE1 published by Ray et al (1988) | | | | | |
| PROPERTIES: | cDNA for tomato fruit pectin esterase | | | | | |
| CGAACTTCTA | AAATGGCTAC | TCCTCAACAA | CCTTTGTTAA | CAAAAACACA | CAAACAAAAT | 60 |
| TCCATAATCA | GCTTCAAGAT | CCTCACTTTT | GTTGTAACTT | TGTTTGTTGC | TCTCTTCTTA | 120 |
| GTTGTGTTTC | TTGTTGCTCC | ATATCAATTT | GAGATTAAAC | ATTCTAATCT | GTGTAAAACT | 180 |
| GCACAAGATT | CCCAACTCTG | TCTCAGTTAT | GTTTCTGATT | TAATATCCAA | TGAAATTGTC | 240 |
| ACATCTGATT | CAGATGGACT | AAGTATTCTG | AAGAAATTTT | TAGTTTACTC | TGTTCATCAA | 300 |
| ATGAACAATG | CAATTCCAGT | GGTTCGCAAA | ATCAAGAATC | AGATCAATGA | CATTCGTGAA | 360 |

TABLE 2-continued

| | | | | | | |
|---|---|---|---|---|---|---|
| CAAGGGGCTT | TAACTGATTG | TCTTGAGCTT | CTTGATCTGT | CAGTTGATTT | AGTATGTGAT | 420 |
| TCAATTGCAG | CAATTGATAA | GAGAAGTCGT | TCGGAGCATG | CCAATGCGCA | AAGTTGGCTA | 480 |
| AGTGGTGTGC | TTACTAACCA | CGTTACGTGC | TTGGATGAGC | TTGATTCCTT | TACTAAAGCT | 540 |
| ATGATAAATG | GAACGAATCT | TGATGAGTTG | ATCTCGAGAG | CTAAGGTAGC | ATTGGCGATG | 600 |
| CTTGCGTCTG | TGACAACTCC | AAATGATGAA | GTTTTGAGGC | CGGGTTTAGG | AAAAATGCCA | 660 |
| TCTTGGGTGA | GTTCGAGGGA | TAGGAAGCTG | ATGGAGAGTT | CGGGTAAGGA | CATTGGAGCG | 720 |
| AATGCAGTGG | TGGCAAAAGA | TGGAACAGGG | AAATATCGAA | CACTTGCTGA | AGCTGTTGCT | 780 |
| GCAGCACCAG | ATAAGAGTAA | GACGCGTTAT | GTAATTTATG | TAAAGAGGGG | AACTTATAAA | 840 |
| GAGAATGTTG | AGGTGAGTAG | CAGGAAAATG | AATTTGATGA | TTATTGGTGA | TGGCATGTAT | 900 |
| GCTACCATCA | TTACTGGGAG | CCTTAATGTT | GTCGATGGAT | CAACAACCTT | CCACTCTGCC | 960 |
| ACTCTTGCTG | CAGTTGGCAA | AGGATTTATA | CTACAGGACA | TATGTATACA | GAACACAGCA | 1020 |
| GGACCAGCTA | AACACCAAGC | TGTTGCACTT | CGAGTTGGAG | CTGATAAGTC | TGTCATAAAT | 1080 |
| CGTTGTCGTA | TCGATGCTTA | TCAAGACACC | CTTTATGCAC | ATTCTCAAAG | GCAATTCTAT | 1140 |
| CGAGACTCCT | ACGTGACAGG | GACTATTGAT | TTCATATTCG | GTAATGCAGC | AGTTGTATTC | 1200 |
| CAGAAATGCC | AGCTCGTAGC | TAGAAAACCG | GGTAAATACC | AGCAAAACAT | GGTGACTGCA | 1260 |
| CAAGGCAGGA | CGGACCCAAA | TCAGGCCACG | GGGACATCAA | TTCAGTTTTG | TGATATAATA | 1320 |
| GCAAGTCCTG | ACCTAAAACC | AGTCGTGAAA | GAATTCCCAA | CATATCTTGG | TAGGCCATGG | 1380 |
| AAAAAATATT | CAAGAACTGT | AGTGATGGAA | TCATCATTGG | GTGGTCTCAT | TGATCCATCG | 1440 |
| GGTTGGGCTG | AGTGGCACGG | AGATTTTGCG | TTAAAGACAT | TGTATTATGG | TGAATTTATG | 1500 |
| AATAATGGAC | CTGGTGCTGG | TACTAGTAAG | CGTGTCAAGT | GGCCTGGCTA | TCATGTCATT | 1560 |
| ACTGACCCCG | CTGAAGCTAT | GTCATTCACT | GTGGCTAAGC | TGATTCAGGG | CGGATCATGG | 1620 |
| TTGAGGTCTA | CTGACGTGGC | GTATGTGGAT | GGATTATATG | ATTAGAGTGA | TATAAAATTA | 1680 |
| CTCTTTGTTT | ATGTAACAAG | ACATCTTTAA | AAAGTTCAAA | GTAAGTAGTA | GTAATATATC | 1740 |
| CATATGAAGT | GCCACATGAG | CAGGGCAGAG | CCGGGATTAA | GTGTCTAAAG | CATAACACAC | 1800 |
| AACTCTAGTG | TGACAAGCAT | TTACATGGCT | CATTCCTTAC | TACTAAGTCG | TCAATAAGTT | 1860 |
| CAGTTAAGGG | GTTCATAAGT | TAATATACGT | ATATATATTT | ATGTTGGCGA | TAAAGCTGAA | 1920 |
| ACTGATGATG | CTTTAATGTA | ATTATAGTTT | TCTGAAAAAG | GATATGTGTA | ATATTAGGTT | 1980 |
| TTCCCTGATG | TTTATGGTTG | TGGGGTGGTG | GTTATGATAA | AAATATGCAA | GATGAAAGTC | 2040 |
| AAAAAAAAAA | AAAAAAAA | | | | | 2059 |

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1990 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| TTGCAAACTT | CTAAAATGGC | TAATCCTCAA | CAACCTTTGT | TAATAAAAAC | ACACAAACAA | 60 |
| AATCCAATAA | TCAGCTTCAA | GATCCTCAGT | TTTGTTATAA | CTTTGTTTGT | TGCTCTCTTC | 120 |
| TTAGTTGCTC | CATATCAAGT | TGAGATTAAA | CATTCTAATC | TATGTAAAAC | TGCACAAGAT | 180 |
| TCCCAACTCT | GTCTCAGTTA | TGTCTCTGAT | TTGATATCCA | ATGAAATTGT | CACAACAGAA | 240 |
| TCAGATGGAC | ATAGTATTCT | GATGAAATTT | TAGTTAACT | ATGTCCATCA | AATGAACAAT | 300 |
| GCAATTCCAG | TGGTTCGCAA | AATGAAGAAT | CAGATCAATG | ACATTCGTCA | ACACGGGGCT | 360 |
| TTAACTGATT | GTCTTGAGCT | TCTTGATCAG | TCAGTTGATT | TCGCATCTGA | TTCAATTGCA | 420 |
| GCAATTGATA | AAAGAAGTCG | CTCGGAGCAT | GCCAATGCGC | AAAGTTGGCT | AAGTGGTGTG | 480 |
| CTTACTAACC | ACGTTACGTG | CTTGGATGAG | CTTGATTCCT | TTACTAAAGC | TATGATAAAT | 540 |
| GGAACGAATC | TTGAAGAGTT | GATCTCGAGA | GCTAAGGTAG | CATTAGCGAT | GCTTGCGTCT | 600 |
| TTGACAACTC | AGGATGAGGA | TGTTTTCATG | ACGGTTTTAG | GAAAAATGCC | ATCTTGGGTG | 660 |
| AGTTCGATGG | ATAGGAAGCT | GATGGAGAGT | TCGGGTAAGG | ACATTATAGC | GAATGCAGTG | 720 |
| GTGGCACAAG | ATGGAACGGG | GGATTATCAA | ACACTTGCTG | AAGCAGTTGC | TGCAGCACCA | 780 |

| | | | | | | |
|---|---|---|---|---|---|---|
|GATAAGAGTA|AGACGCGTTA|TGTAATTTAT|GTAAAGAGGG|GAACTTATAA|AGAGAATGTT|840|
|GAGGTGGCTA|GCAATAAAAT|GAACTTGATG|ATTGTTGGTG|ATGGAATGTA|TGCTACGACC|900|
|ATTACTGGTA|GCCTTAATGT|TGTCGATGGA|TCAACAACCT|TCCGCTCTGC|CACTCTTGCT|960|
|GCAGTCGGCC|AAGGATTTAT|ACTACAGGAC|ATATGTATAC|AGAACACAGC|AGGGCCAGCG|1020|
|AAAGACCAAG|CAGTGGCACT|TCGAGTTGGA|GCTGATATGT|CTGTCATAAA|TCGTTGTCGT|1080|
|ATCGATGCTT|ATCAAGACAC|CCTTTATGCA|CATTCTCAAA|GGCAATTCTA|TCGAGACTCC|1140|
|TACGTGACAG|GTACTGTTGA|TTTCATATTT|GGTAATGCAG|CAGTTGTATT|CCAGAAATGC|1200|
|CAGCTCGTAG|CTAGAAAACC|GGGTAAATAC|CAGCAAAACA|TGGTGACTGC|ACAAGGCAGG|1260|
|ACGGACCCAA|ATCAGGCCAC|GGGGACATCA|ATTCAGTTCT|GTAACATAAT|AGCAAGTTCG|1320|
|GACCTAGAAC|CAGTCCTGAA|AGAATTCCCA|ACATATCTTG|GTAGGCCATG|GAAAGAATAT|1380|
|TCAAGAACTG|TAGTGATGGA|ATCATACTTA|GGTGGTCTCA|TTAATCCAGC|GGGTTGGGCT|1440|
|GAGTGGGACG|GAGATTTTGC|GTTGAAGACA|TTGTATTATG|GTGAATTTAT|GAACAATGGA|1500|
|CCTGGTGCTG|GTACTAGTAA|GCGTGTCAAG|TGGCCTGGTT|ATCATGTCAT|TACTGATCCC|1560|
|GCTAAAGCTA|TGCCGTTCAC|TGTGGCTAAG|CTGATTCAGG|GCGGATCATG|GTTGAGGTCT|1620|
|ACTGGCGTGG|CGTATGTGGA|TGGATTATAT|GATTAGAGTA|TATATATGAT|GTGCCACATG|1680|
|AGCAGGGCAG|AGCAAGCATA|ACACACAACT|CTAGTGTGAC|AAGCATTTAC|ATGGCTCATT|1740|
|CGTTACTACT|AAGTTGTCAA|TAAGTTCTGT|TTAGGGGTTC|ATAAGTTTAT|ATACGTATAT|1800|
|ACATTTACAT|TGGTGATGAA|GCTGAAACTG|ATGATGCTTT|AATGTAATTA|TAGTTTTCTG|1860|
|AAAAAGGATA|TGAGTAATAT|TAGTTTTTCC|CAGATGTGTA|TGGTTGTGGA|ACTGTTTATG|1920|
|CTTAAATTGG|CAAGGGGTAT|TGAATAAAAA|TCTATTGTGT|TAAAAAAAAA|AAAAAAAAA|1980|
|AAAAAAAAAA| | | | | |1990|

( 2 ) INFORMATION FOR SEQ ID NO:2:

( i ) SEQUENCE CHARACTERISTICS:
        ( A ) LENGTH: 2059 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
|CGAACTTCTA|AAATGGCTAC|TCCTCAACAA|CCTTTGTTAA|CAAAAACACA|CAAACAAAAT|60|
|TCCATAATCA|GCTTCAAGAT|CCTCACTTTT|GTTGTAACTT|TGTTTGTTGC|TCTCTTCTTA|120|
|GTTGTGTTTC|TTGTTGCTCC|ATATCAATTT|GAGATTAAAC|ATTCTAATCT|GTGTAAAACT|180|
|GCACAAGATT|CCCAACTCTG|TCTCAGTTAT|GTTTCTGATT|TAATATCCAA|TGAAATTGTC|240|
|ACATCTGATT|CAGATGGACT|AAGTATTCTG|AAGAAATTTT|TAGTTTACTC|TGTTCATCAA|300|
|ATGAACAATG|CAATTCCAGT|GGTTCGCAAA|ATCAAGAATC|AGATCAATGA|CATTCGTGAA|360|
|CAAGGGGCTT|TAACTGATTG|TCTTGAGCTT|CTTGATCTGT|CAGTTGATTT|AGTATGTGAT|420|
|TCAATTGCAG|CAATTGATAA|GAGAAGTCGT|TCGGAGCATG|CCAATGCGCA|AGTTGGCTA|480|
|AGTGGTGTGC|TTACTAACCA|CGTTACGTGC|TTGGATGAGC|TTGATTCCTT|TACTAAAGCT|540|
|ATGATAAATG|GAACGAATCT|TGATGAGTTG|ATCTCGAGAG|CTAAGGTAGC|ATTGGCGATG|600|
|CTTGCGTCTG|TGACAACTCC|AAATGATGAA|GTTTTGAGGC|CGGGTTTAGG|AAAAATGCCA|660|
|TCTTGGGTGA|GTTCGAGGGA|TAGGAAGCTG|ATGGAGAGTT|CGGGTAAGGA|CATTGGAGCG|720|

-continued

| | | | | | | |
|---|---|---|---|---|---|---|
| AATGCAGTGG | TGGCAAAAGA | TGGAACAGGG | AAATATCGAA | CACTTGCTGA | AGCTGTTGCT | 780 |
| GCAGCACCAG | ATAAGAGTAA | GACGCGTTAT | GTAATTTATG | TAAAGAGGGG | AACTTATAAA | 840 |
| GAGAATGTTG | AGGTGAGTAG | CAGGAAAATG | AATTTGATGA | TTATTGGTGA | TGGCATGTAT | 900 |
| GCTACCATCA | TTACTGGGAG | CCTTAATGTT | GTCGATGGAT | CAACAACCTT | CCACTCTGCC | 960 |
| ACTCTTGCTG | CAGTTGGCAA | AGGATTTATA | CTACAGGACA | TATGTATACA | GAACACAGCA | 1020 |
| GGACCAGCTA | AACACCAAGC | TGTTGCACTT | CGAGTTGGAG | CTGATAAGTC | TGTCATAAAT | 1080 |
| CGTTGTCGTA | TCGATGCTTA | TCAAGACACC | CTTTATGCAC | ATTCTCAAAG | GCAATTCTAT | 1140 |
| CGAGACTCCT | ACGTGACAGG | GACTATTGAT | TTCATATTCG | GTAATGCAGC | AGTTGTATTC | 1200 |
| CAGAAATGCC | AGCTCGTAGC | TAGAAAACCG | GGTAAATACC | AGCAAAACAT | GGTGACTGCA | 1260 |
| CAAGGCAGGA | CGGACCCAAA | TCAGGCCACG | GGGACATCAA | TTCAGTTTTG | TGATATAATA | 1320 |
| GCAAGTCCTG | ACCTAAAACC | AGTCGTGAAA | GAATTCCCAA | CATATCTTGG | TAGGCCATGG | 1380 |
| AAAAAATATT | CAAGAACTGT | AGTGATGGAA | TCATCATTGG | GTGGTCTCAT | TGATCCATCG | 1440 |
| GGTTGGGCTG | AGTGGCACGG | AGATTTTGCG | TTAAAGACAT | TGTATTATGG | TGAATTTATG | 1500 |
| AATAATGGAC | CTGGTGCTGG | TACTAGTAAG | CGTGTCAAGT | GGCCTGGCTA | TCATGTCATT | 1560 |
| ACTGACCCCG | CTGAAGCTAT | GTCATTCACT | GTGGCTAAGC | TGATTCAGGG | CGGATCATGG | 1620 |
| TTGAGGTCTA | CTGACGTGGC | GTATGTGGAT | GGATTATATG | ATTAGAGTGA | TATAAAATTA | 1680 |
| CTCTTTGTTT | ATGTAACAAG | ACATCTTTAA | AAAGTTCAAA | GTAAGTAGTA | GTAATATATC | 1740 |
| CATATGAAGT | GCCACATGAG | CAGGGCAGAG | CCGGGATTAA | GTGTCTAAAG | CATAACACAC | 1800 |
| AACTCTAGTG | TGACAAGCAT | TTACATGGCT | CATTCCTTAC | TACTAAGTCG | TCAATAAGTT | 1860 |
| CAGTTAAGGG | GTTCATAAGT | TAATATACGT | ATATATATTT | ATGTTGGCGA | TAAAGCTGAA | 1920 |
| ACTGATGATG | CTTTAATGTA | ATTATAGTTT | TCTGAAAAAG | GATATGTGTA | ATATTAGGTT | 1980 |
| TTCCCTGATG | TTTATGGTTG | TGGGGTGGTG | GTTATGATAA | AAATATGCAA | GATGAAAGTC | 2040 |
| AAAAAAAAA | AAAAAAAA | | | | | 2059 |

We claim:

1. A DNA construct comprising a DNA sequence of the gene encoded by the clone pB8 (SEQ ID NO:1) under the control of a transcriptional initiation region in plants, so that the construct can generate RNA in plant cells.

2. The DNA construct as claimed in claim 1 comprising a transcriptional initiation region operative in plants positioned for transcription of a DNA sequence encoding RNA complementary to a sequence of bases of mRNA of the gene encoded by the clone pB8 (SEQ ID NO:1).

3. The DNA construct as claimed in claim 1 in which the transcriptional initiation region operative in plants is a constitutive promoter.

4. The DNA construct as claimed in claim 3 in which the constitutive promoter is CaMV35S.

5. The DNA construct as claimed in claim 1 in which the transcriptional initiation region operative in plants is an inducible or developmentally regulated promoter.

6. The DNA construct as claimed in claim 5 in which the promoter is that for the polygalacturonase gene.

7. Plant cells transformed with a construct claimed in claim 1.

8. Plant cells claimed in claim 7 which are cells of tomato.

9. Plant cells claimed in claim 7 which are cells of mangoes, peaches, apples, pears, bananas, melons or strawberries.

10. Plants containing cells claimed in claim 7.

11. Plants claimed in claim 10 which bear climacteric fruit.

12. Fruit or seeds of plants claimed in claim 11.

13. Tomato seeds as claimed in claim 12 containing a construct adapted to express RNA antisense to mRNA expressed by the gene encoded by the clone pB8 (Sequence ID No 1).

14. Recombinant DNA comprising SEQ ID NO:1.

15. Recombinant DNA comprising a base sequence at least 16 bases in length that is identical to the sequence from base 16 to base 1654 shown in SEQ ID NO:1 or to the sequence from base 13 to base 367 shown in SEQ ID NO:2.

16. A DNA construct comprising a DNA sequence of clone pB8 (SEQ ID NO:1), or a gene encoding the same amino acid sequence as said DNA sequence, under the control of a transcriptional initiation region in plants, so that the construct can generate RNA in plant cells.

* * * * *